(12) United States Patent
Du et al.

(10) Patent No.: US 8,609,380 B2
(45) Date of Patent: Dec. 17, 2013

(54) SULFIDE GENERATION PROCESS AND SYSTEM FOR SYNGAS FERMENTATION

(75) Inventors: Jianxin Du, Naperville, IL (US); Rathin Datta, Chicago, IL (US)

(73) Assignee: Coskata, Inc., Warrenville, IL (US)

( * ) Notice: Subject to any disclaimer, the term of this patent is extended or adjusted under 35 U.S.C. 154(b) by 0 days.

(21) Appl. No.: 13/345,444

(22) Filed: Jan. 6, 2012

(65) Prior Publication Data

US 2013/0177957 A1   Jul. 11, 2013

(51) Int. Cl.
*C12P 7/06* (2006.01)

(52) U.S. Cl.
USPC .......................................... 435/160; 435/157

(58) Field of Classification Search
USPC .................................................. 435/160, 157
See application file for complete search history.

(56) References Cited

U.S. PATENT DOCUMENTS

| | | | |
|---|---|---|---|
| 4,579,727 A * | 4/1986 | Cronkright et al. | ........ 423/576.4 |
| 5,134,944 A | 8/1992 | Keller et al. | |
| 5,266,024 A | 11/1993 | Anderson | |
| 6,471,937 B1 | 10/2002 | Anderson et al. | |
| 7,285,402 B2 | 10/2007 | Gaddy et al. | |
| 2008/0244976 A1 | 10/2008 | Paisley | |
| 2009/0017514 A1 * | 1/2009 | Datta et al. | ..................... 435/170 |
| 2009/0215163 A1 | 8/2009 | Tsai | |
| 2011/0059499 A1 | 3/2011 | Simpson et al. | |
| 2011/0104770 A1 * | 5/2011 | Tobey | ........................... 435/140 |
| 2011/0229947 A1 | 9/2011 | Zahn et al. | |

OTHER PUBLICATIONS

Klasson et al., Biotechnology for the production of clean fuels, Washington, D.C., Aug. 28, 1990.*

* cited by examiner

*Primary Examiner* — Susan Hanley
*Assistant Examiner* — Damon B Bowe (57) ABSTRACT

A process that generates sulfide in production of liquid products from syngas and a system for syngas fermentation including a sulfide generation process to convert feed gas to liquid product, the process including: partially oxidizing high-temperature gas, input gas, and molten sulfur to generate sulfide gas, the high-temperature gas containing oxygen, the input gas containing carbonaceous fuel and the sulfide gas containing hydrogen sulfide, CO, $CO_2$, and $H_2$; mixing the sulfide gas with the feed gas to generate mixed gas having a predetermined hydrogen sulfide concentration; providing at least a portion of the mixed gas to a production fermentor containing microorganisms; and converting the mixed gas to the liquid product by contact with the microorganisms.

13 Claims, 2 Drawing Sheets

Fig. 2

SULFIDE GENERATION PROCESS AND SYSTEM FOR SYNGAS FERMENTATION

FIELD OF THE INVENTION

This invention relates to syngas fermentation, particularly, a sulfide generation process and system for syngas fermentation to convert feed gas to liquid product.

DETAILED DESCRIPTION

Background

Biofuels production for use as liquid motor fuels or for blending with conventional gasoline or diesel motor fuels is increasing worldwide. Such biofuels include, for example, ethanol, propanol, and n-butanol. One of the major drivers for biofuels is their derivation from renewable resources by bioprocess technology. Biofuels are conventionally made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses, and other agricultural residues may become viable feedstocks for biofuel production. The heterogeneous nature of lignocellulosic materials, which enables them to provide the mechanical support structure of the plants and trees, makes them inherently recalcitrant to bioconversion. These materials predominantly contain three separate classes of components as building blocks: cellulose ($C_6$ sugar polymers), hemicellulose (various $C_5$ and $C_6$ sugar polymers), and lignin (aromatic and ether linked hetero polymers).

Breaking down these recalcitrant structures to provide fermentable sugars for bioconversion to ethanol typically requires pretreatment steps together with chemical/enzymatic hydrolysis. Conventional yeasts are unable to ferment the $C_5$ sugars to ethanol, and lignin components are completely unfermentable by such organisms. Lignin often accounts for 25 to 30 percent of the mass content and 35 to 45 percent of the chemical energy content of lignocellulosic biomass. For these reasons, processes based on a pretreatment/hydrolysis/fermentation path for conversion of lignocellulose biomass to ethanol are inherently difficult and often involve uneconomical multi-step, multi-conversion processes.

One alternative process is to convert lignocellulosic biomass to syngas and then to ferment syngas with anaerobic microorganisms to produce biofuels, such as ethanol, propanol, and n-butanol, or chemicals, such as acetic acid, butyric acid, and the like. Syngas is also known as synthesis gas, and is primarily a mix of CO, $H_2$, and $CO_2$, with other components such as $H_2S$, low molecular weight hydrocarbons (primarily methane), and other less significant or trace gases. The syngas process can be inherently more efficient than the pretreatment/hydrolysis/fermentation process because the gasification step can convert all of the components to syngas with good efficiency (e.g., greater than 75 percent), and some strains of anaerobic microorganisms can convert syngas to ethanol, propanol, n-butanol, or other chemicals with high efficiency (e.g., greater than 90 percent of theoretical). Thus, syngas is defined as containing at minimum carbon monoxide, hydrogen, and carbon dioxide, and usually contains other components such as water vapor, nitrogen, methane, ammonia, hydrogen sulfide, and the like. (For purposes herein, all gas compositions are reported on a dry basis unless otherwise stated or clear from the context.)

In addition to biomass, syngas can be produced from many other carbonaceous feedstocks, such as natural gas, reformed gas, peat, petroleum coke, coal, solid waste, and land fill gas. Biomass and the other carbonaceous feedstocks are made up primarily of carbon, hydrogen, and some oxygen, but can also contain calcium, potassium, magnesium, sulfur, phosphorus, manganese, zinc, iron, aluminum, sodium, silicon, boron, copper, and other trace elements. The latter elements and related compound contribute to syngas compounds other than CO, $H_2$, and $CO_2$, such as $H_2S$, and/or a gasifier residue, such as ash or slag.

The syngas process requires that the syngas components CO and $H_2$ be efficiently and economically dissolved in the aqueous medium and transferred to anaerobic microorganisms that convert them to the desired products. Also, very large quantities of these gases are required. For example, the theoretical overall equations for ethanol production from syngas are:

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Thus, 6 moles of relatively insoluble gases such as CO and $H_2$ have to transfer to an aqueous medium for each mole of ethanol produced. Other liquid products such as acetic acid, propanol, and n-butanol have similar large stoichiometric requirements for the gases.

The anaerobic microorganisms that bring about these bioconversions generate very little metabolic energy from these bioconversions and require some sulfur to maintain biological activity. Consequently, the relatively slow growth of the microorganisms, which often continue the conversions during the non-growth phase of their life cycle to gain metabolic energy for their maintenance, depends on available sulfur.

Anaerobic fermentations of syngas with acetogenic bacteria to produce C2 to C4 alcohols or organic acids requires sulfur compounds as key nutrients for the acetogenic bacteria. In addition, the primary enzymes of the production pathway have sulfur-containing ligands which are essential to the metabolism of the organisms. The simplest sulfur compound that can be used by many of these organisms is hydrogen sulfide ($H_2S$) or inorganic sulfide salts such as $Na_2S$.

Unfortunately, hydrogen sulfide is a highly toxic gas which presents risks to personnel and the general population should leakage occur. Sulfide salts can release hydrogen sulfide gas under acidic conditions, posing the same risk as hydrogen sulfide gas. Hence, it would be desirable to have a sulfide generation process and system for syngas fermentation able to deliver the desired quantity of hydrogen sulfide gas at a controlled rate for safe and economical operation of a large scale syngas fermentation process without the need to maintain a large inventory of hydrogen sulfide gas, or inorganic sulfide salts.

It would be desirable to have sulfide generation process and system for syngas fermentation that would overcome the above disadvantages.

SUMMARY OF THE INVENTION

To provide the hydrogen sulfide required for large-scale syngas fermentation without stockpiling hydrogen sulfide gas, molten sulfur can be introduced into a partial oxidation reformer. The molten sulfur is converted at high-temperature and reducing conditions with input gas containing methane to generate sulfide gas containing hydrogen sulfide, CO, $CO_2$, and $H_2$. The sulfide gas can be provided to fermentors containing microorganisms which require the sulfur. The sulfide gas can be supplied directly to the fermentors or can be mixed with feed gas to provide a predetermined hydrogen sulfide concentration.

In accordance with this invention processes and systems are provided for the conversion of biomass to oxygenated organic compound using an in-situ hydrogen sulfide generation operation that is cost effective and simplifies the delivery of hydrogen sulfide. The processes and systems of this invention generate the hydrogen sulfide in a partial oxidation reformer to produce a sulfide gas that can go directly to the fermentation process. The partial oxidation reformer provides several advantages beyond simplifying the delivery of hydrogen sulfide. The partial oxidation reformer increases the concentration of carbon monoxide and provides a hydrogen-to-carbon monoxide mole ratio that is particularly advantageous in syngas for anaerobic fermentation. Accordingly, a higher percentage of the biomass becomes available for bioconversion to oxygenated organic compound.

One embodiment of this invention includes generation of sulfide containing gas in a process to convert feed gas to liquid product, the process including: partially oxidizing high-temperature gas, input gas, and molten sulfur to generate sulfide gas, the high temperature gas containing oxygen, the input gas comprising a carbonaceous fuel, preferably methane or syngas, and the sulfide gas containing hydrogen sulfide, CO, $CO_2$, and $H_2$; mixing the sulfide gas with the feed gas to generate mixed gas having a predetermined hydrogen sulfide concentration; providing at least a portion of the mixed gas to a production fermentor containing microorganisms; and converting the mixed gas to the liquid product by contact with the microorganisms.

Another embodiment of this invention includes a system to convert feed gas to liquid product, the system including: a partial oxidation reformer operable to partially oxidize high-temperature gas, input gas, and molten sulfur to generate sulfide gas, the high temperature gas containing oxygen, the input gas containing a carbonaceous fuel and the sulfide gas containing hydrogen sulfide, CO, $CO_2$, and $H_2$; a mixer operably connected to receive the sulfide gas from the partial oxidation reformer and operable to mix the sulfide gas with the feed gas to generate mixed gas having a predetermined hydrogen sulfide concentration; and a production fermentor containing microorganisms operably connected to receive at least a portion of the mixed gas and operable to convert the mixed gas to the liquid product by contact with the microorganisms.

Yet another embodiment of this invention includes a process to convert syngas feed to a $C_1$ to $C_4$ liquid product, the process including: combusting oxygen and burner gas to generate high-temperature gas containing oxygen; partially oxidizing a methane containing gas with the high-temperature gas and adding molten sulfur to generate sulfide gas, the sulfide gas containing hydrogen sulfide, CO, $CO_2$, and $H_2$; mixing the sulfide gas with the syngas feed to generate mixed gas having a predetermined hydrogen sulfide concentration; providing at least a portion of the mixed gas to a production fermentor containing microorganisms; and converting the mixed gas to the liquid product by contact with the microorganisms.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof. The description of the invention in a particular context does not restrict its application or claim coverage from other process applications that meet the criteria for its use.

DETAILED DESCRIPTION OF THE INVENTION

Definitions

As used herein, unless otherwise stated, compositions of gases are on an anhydrous basis.

Oxygenated organic compound means one or more organic compounds containing two to six carbon atoms selected from the group of aliphatic carboxylic acids, alkanols, and aldehydes.

Biomass means biological material living or recently living plants and animals and contains at least hydrogen, oxygen, and carbon. Biomass typically also contains nitrogen, phosphorus, sulfur, sodium, and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagasse), and the like; and waste such as garbage and municipal waste. Biomass does not include fossil fuels such as coal, natural gas, and petroleum.

The abbreviation ppm means parts per million. Unless otherwise stated or clear from the context, ppm is on a mole basis (ppm (mole)).

Stable gas-in-liquid dispersion means a mixture of gas bubbles in liquid where (i) the bubbles predominantly flow in the same direction as the liquid, and (ii) the dispersion is sufficiently stable that it exists throughout the aqueous menstruum, i.e., insufficient coalescing of bubbles occurs to destroy the dispersion.

Biomass Gasification

The processes and systems of this invention will typically receive syngas from a gasification process. Gasification is a thermal process to convert biomass. The gasification may be effected by any suitable process to provide a gas containing carbon monoxide and hydrogen and may involve the presence of controlled amounts of oxygen and steam. Typically gasification involves heating the biomass in an oxygen-controlled environment. The heat may be provided by direct or indirect heat exchange as stated above. Various types of gasifiers include pyrolysis, counter current fixed bed, co-current fixed bed, moving bed, fluidized bed, entrained flow, and plasma gasifiers. One type of gasification process is the Taylor gasification process generally disclosed in U.S. Published Patent Application No. 2008/024496 A1, hereby incorporated by reference in its entirety. The process may involve a combination of pyrolysis and steam reforming. In accordance with this invention, gasification occurs at a temperature of at least about 450° C., often between about 500° C. and 1500° C., say, 600° C. to 1250° C. The gasification may be conducted at any suitable pressure including subatmospheric pressure, but is typically conducted at pressures from about 100 to 5000 KPa absolute.

The gasification may be a direct, indirect, or partially direct gasification. An indirect gasification does not use free oxygen, but an external source of heat is required. Direct gasification occurs where oxygen is used to partially oxidize the biomass. In the processes of this invention, the gasification is conducted by supplying the heat for gasification at least partially in an indirect mode. Syngas will typically have a mole ratio of hydrogen to carbon monoxide between about 0.4:1 to 1.5:1, preferably between about 0.8:1 and 1.3:1, and wherein hydrogen and carbon monoxide comprise at least about 70, preferably at least about 75, and most preferably at least about 80, mole percent of the syngas composition. The syngas may also contain carbon dioxide in a mole concentration of between 3 and 15 mole percent and methane in a concentration of between 3 and 15 mole percent. In most cases the syngas will also contain water and nitrogen. The amount of nitrogen will, in part, depend upon the composition of the feedstock, nature of the gasification process, and the oxygen-containing gas used for the partial oxidation. Where an indirect gasification process is used and partial oxidation is conducted using an oxygen-containing gas having a high molecular oxygen content, the nitrogen content can be relative low, say, from about 0.1 to 5 mole percent of the of the syngas. Direct gasification processes using air and partial oxidation processes using air, can yield a syngas with nitrogen concentrations as high as 55 to 60 mole percent of the syngas. The preferred composition of the mixed gas that enters the fermentor will contain at least about 20, often between about 80 and 300, ppm(mole) hydrogen sulfide.

The gasification of biomass results in the formation of ash (including char) and at least some of the ash will be entrained in the crude syngas. The amount of these solids present in the crude syngas will depend not only upon the type of gasifier used but also the nature of the biomass. The processes of this invention comprise removing at least about 75, preferably at least about 90 to essentially 100, mass percent of the solids from the crude syngas. The removal of solids can be effected in any suitable manner. Cyclones are preferred since in most instances, cyclones are capable of removing sufficient entrained solids.

The solids removed from the crude syngas and any solids removed from the gasifier usually contain non-volatilized tars. If desired, additional heat and syngas values can be recovered by subjecting these solids to oxidation conditions preferably including temperatures of at least about 700° C. and the presence of oxygen-containing gas such as air especially where heating values are sought, or oxygen or oxygen enriched air where additional syngas is sought to be produced without undue nitrogen content.

Partial Oxidation

Since the partial oxidation zone contains sulfur compounds, the partial oxidation is preferably conducted in a non-catalytic manner. The partial oxidation is typically conducted at a temperature in the range of between about 800° C. to 1700° C., preferably the partial oxidation is conducted at a temperature of at least 1000° C., preferably between 1150° C. and 1500° C. Generally the partial oxidation is substantially adiabatic, and thus the targeted temperature will be achieved by a combination of the temperatures, duration of the partial oxidation and relative mass flow rates of the input gases and the heat generated by the partial oxidation. All else being substantially the same, lower partial oxidation temperatures tend to result in higher hydrocarbon concentrations in the partially-oxidized syngas and higher partial oxidation temperatures tend to result in higher carbon dioxide concentrations in the sulfide gas.

The partial oxidation may be conducted at subatmospheric, atmospheric, or superatmospheric pressure. Typically the pressure used for the partial oxidation is in the range of between about 100 and 3000, preferably between about 100 and 500, KPa absolute. The conditions of the partial oxidation are preferably such that combustion is avoided or mitigated. Often the velocity of the total gases during partial oxidation is sufficiently high to avoid a flame front, for instance, at least about 150, preferably at least about 200, say, between about 250 and 500, meters per second. At these partial oxidation conditions, the partial oxidation can be conducted relatively rapidly.

The partial oxidation reformer may have one or more ports for the introduction of each of the high temperature gas, the input gas, and the molten sulfur. A partial oxidation reformer may comprise a static mixer to facilitate mixing of the high temperature gas, the carbonaceous fuel, and the molten sulfur.

The high temperature gas that enters the partial oxidation reformer is an oxygen-containing gas that admixed with the carbonaceous fuel for purposes of the partial oxidation. The source of the oxygen may be air, oxygen-enriched air, or substantially pure oxygen. Where it is desired to avoid undue nitrogen dilution of the syngas, the source of the oxygen for the oxygen-containing gas preferably contains at least about 75, preferably at least about 90, and most preferably at least about 98, mole percent oxygen (concentration including the presence of nitrogen but is on an anhydrous basis). The oxygen-containing gas prior to contacting the carbonaceous fuel and sulfur may contain components other than oxygen and nitrogen, including, but not limited to, hydrogen, carbon monoxide, carbon dioxide, hydrocarbon-containing compounds (preferably hydrocarbon-containing compounds having between about 1 and 20 carbons), and water vapor. The amount of oxygen provided is sufficient to provide the sought partial oxidation temperature.

The amount of oxygen required for a specific sulfide gas composition will also depend upon the composition of the carbonaceous fuel and the extent that any additional fuel is desired to be converted into incrementally additional syngas. In general, the mass ratio of oxygen to any added hydrocarbon fuel is between about 0.3:1 to 3.5:1.

The partial oxidation comprises adding a carbonaceous fuel to a partial oxidation reformer. The terms "carbonaceous fuel" and "fuel" as used herein refer to fuels that contain hydrogen and carbon atoms and may contain hetero atoms including, but not limited to oxygen and nitrogen atoms. While syngas can be used as the fuel, typically hydrocarbon-containing fuels are less expensive than syngas. When syngas is used in the partial oxidation step, the invention benefits from having a crude syngas feed that is already at an elevated temperature, i.e., at a temperature of at least about 350° C. Combustion of the fuel provides heat to provide the sought partial oxidation temperature. Carbonaceous fuels include, but are not limited to, natural gas, propane, liquified petroleum gas, butane, fuel oil, petroleum fractions having normal boiling points between about 35° C. and 350° C., and oxygenated hydrocarbons such as alkanols (such as methanol, ethanol, propanol, and butanol), diols (such as ethylene glycol), esters, ethers, and carboxylic acids of 1 to 20 carbons.

The preferred carbonaceous fuel is a methane containing stream such as natural gas. The amount of fuel added will, in part, depend upon the amount of heat necessary to be generated to achieve the sought partial oxidation temperature. More carbonaceous fuel can be added, and its partial oxidation will result in the production of additional syngas. The amount of carbonaceous fuel added is at least about 3:1, more often at least about 4:1, and sometimes between about 5:1 and 10:1, for instance, 5:1 to 6:1, mass percent of the oxygen entering the partial oxidation reformer zone.

Preferably the high temperature gas is generated by oxidation of the oxygen containing stream in admixture with a burner gas in an oxygen burner. The oxygen containing stream may be air or air enriched with oxygen. Where the heating of the high temperature gas in the oxygen burner is conducted using oxygen enriched air or oxygen, the oxygen-containing gas mixed with the burner gas has an oxygen content of at least about 50, preferably at least about 90, and most preferably at least about 98, mole percent oxygen. The burner gas may comprise hydrogen or any light hydrocarbon that enters the oxygen burner in gaseous phase. Typically the burner gas will comprise a $C_1$ to $C_4$ alkane. Methane is a preferred burner gas and will usually be provided as natural gas.

The oxygen burner may be under the same or different conditions than those for the partial oxidation reformer. The pre-reaction may be catalytic or non-catalytic. The oxygen burner provides the heat necessary to raise the high temperature gas to its desired temperature. Typically the high temperature gas will have a temperature of at least 1000° C. and more preferably will have a temperature in the range of 1500 to 2500° C. Examples of types of apparatus for providing and pre-reacting the fuel/oxygen admixture are disclosed in U.S. Pat. Nos. 5,266,024 and 6,471,937, both herein incorporated by reference in their entireties.

Preferably the partial oxidation conditions are selected to adjust the hydrogen to carbon monoxide mole ratio and to decrease the concentration of carbon dioxide in the syngas. In part, these results are obtained by a reverse water gas shift. In general, partial oxidation conditions wherein higher input hydrocarbon (from the crude syngas and potentially the added hydrocarbon fuel) is increased, higher hydrogen to carbon monoxide ratios are obtained, all else being maintained substantially constant. The mole ratio of hydrogen to carbon monoxide in the partially-oxidized syngas is often between about 0.4:1 to 1.5:1, preferably between about 0.8:1 and 1.3:1. For many anaerobic fermentation microorganisms, carbon monoxide is a preferred substrate for bioconversion to oxygenated organic compound. Moreover, the partial oxidation provides a net increase in this substrate not only because of the conversion of hydrocarbons but also due to the reverse water gas shift. Preferably the partial oxidation of the input gas in the presence of the molten sulfur is non-catalytic.

Sulfide Gas

The partial oxidation reformer requires a relatively small amount of molten sulfur to provide the needed hydrogen sulfide in the sulfide gas. Relative volumes of the hydrogen sulfide gas that gets mixed with syngas or any other feed gas will determine the necessary concentration of the hydrogen sulfide needed in the sulfide gas. The concentration of hydrogen sulfide in the sulfide gas will usually be in a range of from 200 to 5,000 ppm (mole) hydrogen sulfide. Thus the amount of molten sulfur entering the partial oxidation reformer is very low in relation to the high temperature gas and input gas. Any suitable system can be used to supply molten sulfur to the partial oxidation reformer. In such systems a storage tank will typically store a volume of molten sulfur at temperature in a range of 120 to 150° C. for injection into the partial oxidation reformer. A pump or other metering device can inject the sulfur into the partial oxidation reformer at one or more injection points. Vaporization and/or reduction of the molten sulfur will quickly take place at the high temperature of the partial oxidation reformer.

Sulfide Gas Cooling

The sulfide gas either separately or together as part of the mixed gas will undergo cooling before entering the fermentation zone. The cooling may involve one or more unit operations. Advantageously due to the high temperature of the sulfide gas or the mixed gas, heat in these streams is typically recovered in a steam boiler to provide steam supply for the biomass conversion process. Preferably, the steam generated is at a pressure of between about 750 and 1500, say, 900 to 1100, KPa absolute and the temperature of the sulfide gas or mixed gas is reduced to between about 120° C. to 180° C. Alternatively, or in addition, the sulfide gas or the mixed gas may be used in indirect heat exchange with other process streams such as syngas passing to the partial oxidation reformer or to heat air used to dry biomass.

The cooling the mixed gas stream or the sulfide gas usually involves at least one direct heat exchange with water. Usually this direct heat exchange occurs only after the mixed gas or sulfide gas has been cooled to a temperature below about 180° C., preferably below about 150° C. The direct heat exchange may involve passing the gas through water or a countercurrent contact with a water spray, and the gas is cooled to a temperature below about 100° C., preferably below about 50° C., and often at a temperature suitable for introduction into a fermentor or for any optional cleanup operation.

The direct heat exchange can also serve to remove a portion of hydrogen sulfide, ammonia, and at least some of the hydrogen cyanide contained in the sulfide gas or mixed gas. The amount of hydrogen cyanide removed can be enhanced by maintaining the cooling water at a pH in the range of about 5.5 to 7.5, say, about 6 to 6.5. Additionally, reactants for hydrogen cyanide such as acetaldehyde can me contained in the cooling water. Accordingly, the direct heat exchange with water can also serve to remove hydrogen cyanide to levels suitable such that the cooled syngas can be introduced into the fermentation operation without further cleanup treatment.

Mixed Gas

The sulfide gas passes into admixture with the feed gas to produce the mixed gas stream. The feed gas can comprise CO or a mixture of $CO_2$ and hydrogen or a syngas stream that comprises a combination of the two. The desired concentration of hydrogen sulfide in the mixed gas and the relative ratio of the feed gas to the sulfide gas will determine the necessary concentration of hydrogen sulfide in the sulfide gas. As previously stated, the concentration of hydrogen sulfide in the mixed gas will typically include at least about 20, often between about 100 and 500, and in some cases up to 1000 ppm (mole) hydrogen sulfide.

Fermentation Gas Feed

The sulfide gas and/or mixed gas, serves as fresh feed to a fermentation vessel or vessels. The mixed gas or sulfide gas may be admixed with other gases, including but not limited to, syngas from other sources and recycled off gas from the fermentation. The syngas from other sources may include, but is not limited to, syngas from another biomass gasifier, syngas made from other sources of hydrocarbon such as natural gas, gas generated by reforming or partial oxidation of hydrocarbon-containing materials, and gas generated during petroleum and petrochemical processing. Thus, the gas fed to a fermentor may have the same or a different composition as the composition of the mixed gas or sulfide gas.

Oxygenated Compound, Microorganisms, and Fermentation Conditions

The oxygenated organic compounds produced in the processes of this invention will depend upon the microorganism used for the fermentation and the conditions of the fermentation. This invention finds ready application to the production of acetic acid, ethanol, and other products from a feed gas stream. One or more microorganisms may be used in the fermentation menstruum to produce the sought oxygenated organic compound. Bioconversions of CO and $H_2/CO_2$ to acetic acid, propanol, butanol, butyric acid, ethanol, and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of *Biochemistry and Physiology of Anaerobic Bacteria*, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," *Journal of Fermentation and Bioengineering*, vol. 72, 1991, p. 58-60; "Production of butanol and ethanol from synthesis gas via fermentation," *FUEL*, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, *Arch Microbiol.*, 1994, 345-351; *Archives of Microbiology* 1994, 161: 345-351; and *Clostridium Coskatii* having the identifying characteristics of ATCC No. PTA-10522, filed as U.S. patent application Ser. No. 12/272,320 on Mar. 19, 2010. All of these references are incorporated herein in their entirety.

Suitable microorganisms for bioconversion of syngas to oxygenated organic compound generally live and grow under anaerobic conditions, meaning that dissolved oxygen is essentially absent from the fermentation liquid. Adjuvants to the aqueous menstruum may comprise buffering agents, trace metals, vitamins, salts etc. Adjustments in the menstruum may induce different conditions at different times such as growth and non-growth conditions which will affect the productivity of the microorganisms. U.S. Pat. No. 7,704,723, hereby incorporated by reference in its entirety, discloses the conditions and contents of suitable aqueous menstruum for bioconversion CO and $H_2/CO_2$ using anaerobic microorganisms.

Anaerobic fermentation conditions include a suitable temperature, say, between 25° and 60° C., frequently in the range of about 30° to 40° C. The conditions of fermentation, including the density of microorganisms, aqueous menstruum composition, and gas feed residence time, are preferably sufficient to achieve the sought conversion efficiency of hydrogen and carbon monoxide, and will vary depending upon the design of the fermentation reactor and its operation. The pressure may be subatmospheric, atmospheric, or super atmospheric, and is usually in the range of from about 90 to 1000 KPa absolute and in some instances higher pressures may be desirable for biofilm fermentation reactors. As most reactor designs, especially for commercial scale operations, provide for a significant height of aqueous menstruum for the fermentation, the pressure will vary within the fermentation reactor based upon the static head.

The fermentation conditions are preferably sufficient to effect at least about 40 or 50 percent conversion of the carbon monoxide in gas feed. For commercial operations, the fermentation operation preferably provides a total molar conversion of hydrogen and carbon monoxide in the net gas feed in the range of about 85 to 95 percent. Due to the low solubilities of carbon monoxide and hydrogen in the aqueous phase, achieving these high conversions may require one or more of using multiple fermentation reactors and recycling off gas from a reactor.

The rate of supply of the gas feed under steady state conditions to a fermentation reactor is such that the rate of transfer of carbon monoxide and hydrogen to the liquid phase matches the rate that carbon monoxide and hydrogen are bioconverted. Hence, the dissolved concentration of carbon monoxide and hydrogen in the aqueous phase remains constant, i.e., does not build-up. The rate at which carbon monoxide and hydrogen can be consumed will be affected by the nature of the microorganism, the concentration of the microorganism in the aqueous menstruum and the fermentation conditions. As the rate of transfer of carbon monoxide and hydrogen to the aqueous menstruum is a parameter for operation, conditions affecting the rate of transfer such as interfacial surface area between the gas and liquid phases and driving forces are important.

To increase the conversion of carbon monoxide and hydrogen in the fresh gas feed to the fermentation, off-gas withdrawn from a fermentation reactor may be recycled or passed to a fermentation reactor that is sequential in gas feed flow. Where off-gas is recycled, the portion of off-gas recycled is generally selected to avoid an undue build-up of the concentration of inerts and other gases in the fermentation reactor.

Fermentation Reactors

The fermentation reactors used in this invention may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors; and static mixer reactors including, but not limited to, pipe reactors.

One preferred type of reactor design uses biofilms. Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. U.S. Published Patent Application No. 2008/0305539; U.S. Published Patent Application No. 2009/0035848; and U.S. Published Patent Application No. 2008/0305540, all hereby incorporated by reference in their entireties, disclose membrane based bioreactors wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO and $H2/CO_2$ to ethanol and other liquid products such as butanol, acetic acid, propanol and butyric acid. In these systems the gas flows through a porous region of a hydrophobic membrane and then reaches a biofilm which is hydrophilic.

U.S. Published Patent Application No. 2009/0215153 A1, hereby incorporated by reference in its entirety, discloses contacting syngas components such as CO or a mixture of $CO_2$ and $H_2$ with a surface of a membrane that contains a biolayer of microorganisms and permeating liquid to and from the opposite side of the membrane will provide a stable system for producing liquid products such as ethanol, butanol, hexanol, and other chemicals. The membrane has an asymmetric construction that provides a porous side, referred to herein as a biolayer that provides pores to promote and control the growth of microorganism colonies therein while also exposing a surface over which to directly feed the microorganisms with syngas. Simultaneously another layer of the asymmetric membrane having less permeability than the biolayer, herein referred to as a hydration layer, permeates liquid from the opposite side of the asymmetric membrane. The liquid products produced in the biolayer on the membrane's gas contact side pass through the membrane and into a liquid stream that recovers the desired liquid products while also supplying nutrients to the biolayer in the reverse direction of liquid product flow.

In membrane type reactors, generally the syngas flows through the gas chamber or channels of the bioreactor system continuously or intermittently. The gas feed gas pressure is in the range of 110 to 7000 KPa absolute, preferably about 150 to 1200 KPa absolute. The differential pressure between the liquid and gas phases is managed in a manner that the membrane integrity is not compromised (e.g., the burst strength of the membrane is not exceeded) and the desired gas-liquid interface phase is maintained.

Particularly suitable forms of asymmetric membranes are porous membranes with a tight (i.e., having small pores) thin "skin" on one surface of the membrane that provides the hydration layer and a relatively open support structure underneath the skin that provides the biolayer and defines the biopores. The skin will typically comprise a semi-permeable layer having a thickness of from 0.5 to 10 μm. The skinned asymmetric membrane can include an "integrally skinned" membrane prepared by using phase inversion of one polymer or a composite membrane, where a thin layer of a certain material is formed on top of a porous sublayer of a same or different material.

Other preferred types of fermentation reactors for commercial scale operations are deep tank reactors in which the microorganisms are suspended in an aqueous menstruum. Deep tank reactors have a sufficient depth of the aqueous menstruum to increase time for mass transfer from the gas to aqueous phase and thereby enhance conversion of carbon monoxide and hydrogen. Most often, deep tank reactors are bubble column reactors, jet loop reactors, and stirred tank reactors. Preferably, stirred tank reactors are mechanically-assisted liquid distribution (MLD) tank reactors, or MLD tank reactors where the stirring is insufficient to generate small bubbles.

Preferably, the gas feed is passed through the deep tank reactors in the form of small bubbles, sometimes microbubbles, to facilitate mass transfer of carbon monoxide and hydrogen. Microbubbles are bubbles having a diameter of 500 microns or less. The deep tank reactor has a height of at least about 10, often between about 10 or 15 and 30, meters and an aspect ratio of height to diameter of at least about 0.5:1, say, between about 0.5:1 to 5:1, preferably between about 1:1 to 3:1.

The microbubbles of gas feed introduced into the aqueous menstruum can be generated by any suitable means including spargers and educers. Preferably, they are generated by injection of the gas feed with a motive liquid. In preferred processes, the gas feed is injected into the deep tank reactor as a relatively stable gas-in-liquid dispersion. The injectors may be jet mixers/aerators or slot injectors. Slot injectors are preferred, one form of which is disclosed in U.S. Pat. No. 4,162, 970. These injectors operate using a motive liquid. The injectors, especially slot injectors, are capable of operating over a wide range of liquid and gas flow rates and thus are capable of significant turn down in gas transfer capability. The use of injectors can provide better control over the size of the gas bubbles being introduced into the aqueous menstruum and thus the interfacial area between the gas and liquid phases. Changing bubble size thus modulates the mass transfer of carbon monoxide and hydrogen to the aqueous menstruum. Additionally, the modulation enables a microbubble size to be generated that results in a preferred, stable gas-in-liquid dispersion.

In a bubble column reactor, the feed gas is introduced at the bottom of the vessel and bubbles through the aqueous menstruum. Bubble column reactors may contain axial-flow promoting devices such as baffles, down draft tubes and the like although these devices add to the capital costs of the reactors. Hence, most bubble column reactors do not contain these devices. While bubble column reactors are typically the most economical design and can provide high conversion efficiencies, other reactor designs may find utility in commercially viable bioconversion facilities. A preferred commercial scale operation using bubble columns uses sequential bubble columns to the gas feed flow. U.S. patent application Ser. No. 13/243,062, filed Sep. 23, 2011, hereby incorporated by reference in its entirety, discloses anaerobic fermentation processes using sequential deep, bubble columns to achieve high conversion of carbon monoxide, and hydrogen contained in the gas feed without incurring carbon monoxide inhibition. The processes comprise the combination of (i) using at least two deep, bubble column reactors in flow series; (ii) using certain feed gas compositions; (iii) introducing the feed gas by injection with a motive liquid to produce microbubbles; and (iv) limiting the degree of conversion of carbon monoxide in the upstream reactor.

The deep MLD tank reactors use one or more mechanical stirrers. The mechanical stirring should be sufficient to promote the uniformity of liquid composition through the reactor and need not, and preferably is not, used as a generator of a significant fraction of the microbubbles. Usually two or more mechanical stirrers are used at different heights with higher aspect ratio reactors. The design of mechanical stirrers for stirred tank reactors and their positioning within the reactors for very large diameter tanks are well within the skill of a stirred tank reactor designer. Side paddles or side mounted mixers with impellers are frequently used. Preferably, the design of the mechanical stirrers and the positioning within the reactor take into consideration energy costs in generating the liquid flow to obtain uniformity of the aqueous menstruum in the reactor. The deep MLD tank reactor may contain baffles or other static flow directing devices. Preferred processes for anaerobic fermentation of syngas to produce oxygenated organic compound are disclosed in U.S. patent application Ser. No. 13/243,426, filed Sep. 23, 2011, hereby incorporated by reference in its entirety.

Preferred start-up procedures for deep tank reactors using injectors to supply the gas feed are disclosed in U.S. patent application Ser. No. 13/243,159, filed Sep. 23, 2011, hereby incorporated by reference in its entirety. The processes involve increasing both the volume of the aqueous menstruum and the density of the microorganism culture in the aqueous menstruum during start up while modulating the supply of gas feed to achieve both robust growth of the microorganism culture while avoiding the risk of carbon monoxide inhibition.

Especially for commercial scale operations, it may be desired to pre-react the gas feed to a deep tank reactor to reduce the risk of carbon monoxide inhibition. The pre-reactor may be of any suitable configuration including, but not limited to, bubble column reactors, especially bubble column reactors having an aqueous menstruum height of less than about 10 meters, preferably less than about 5 meters; jet loop reactors; stirred tank reactors; trickle bed reactors; biofilm reactors; and static mixer reactors including, but not limited to, pipe reactors. The pre-reaction often converts between about 10 and 40 percent of the carbon monoxide in the gas feed to oxygenated organic compound. A pre-reaction operation is disclosed in U.S. patent application Ser. No. 13/243,347, filed Sep. 23, 2011, hereby incorporated by reference in its entirety.

The invention may be used in conjunction with a seed fermentor. The seed fermentor may be a single vessel in which incremental growth increases the population of microorganisms and provide inoculum for subsequent stages of microorganism growth or supplementation of the microorganism in a commercial fermentor. In typical industrial applications the inoculation of successive phases of the growth process results in a 1:10 increase in the biological population of microorganisms through a series of seed fermentor referred to as a seed train. Therefore the seed fermentor will usually include multiple vessels that successively scale up the available microorganism population in increasingly larger vessels. For example, the seed train may start with a 15 liter vessel that receives a 1 liter volume of inoculum containing a desired microorganism. Once the volume of fermentation menstruum has increased volume to 10 liters, with a corresponding growth of microorganisms, the vessel contents enter a vessel that can retain a 10 fold higher volume of fermentation mentsruum. In such fashion the seed train vessel sizes increase to hold 1000, 10000, and larger volumes of fermentation menstruum.

Conditions with the fermentation vessel, whether an individual vessel or part of a seed train, are selected to nurture growth of the microorganisms. The seed fermentor can receive mixed gas. The seed fermentor may also receive sulfide gas, or a combination of mixed gas and sulfide gas to vary the concentration of hydrogen sulfide entering the seed fermentor from that entering the fermentation vessel used for liquid product production. Conditions that can promote growth include short residence time, pH adjustments, temperature adjustments, adjustments in sulfide concentration, and added nutrients, such as vitamins.

Product Recovery

The fermentation vessel may have added from time to time or continuously one or more streams of water, nutrients or adjuvants, and microorganisms. A portion of the aqueous menstruum is withdrawn from time to time or continuously from the reactor for product recovery. Usually, the withdrawal is made at a point at the upper portion of the aqueous menstruum in the vessel. Product recovery can consist of known equipment arrangements for removal of residual cell material, separation, and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Published Patent Application No. 2009/0215139 A1 shows an arrangement for a product recovery reactor that recovers an ethanol product from a bioreactor, herein incorporated by reference in its entirely.

Carbon Dioxide Removal

Carbon dioxide may be removed from at least one of the aqueous menstruum in a reactor or from the off-gas from a reactor where the off-gas is recycled or passed to a subsequent fermentation reactor. Any suitable carbon dioxide removal process may be used including amine extraction, alkaline salt extractions, water absorption, membrane separation, adsorptions/desorption, and physical absorption in organic solvents. Considerable flexibility exists in the carbon dioxide removal step in that certain amounts of carbon dioxide are to be fed to the sequential reactor. In preferred aspects of the invention, the off-gas after carbon dioxide removal will contain at least about 15, say, between 15 and 50, mole percent of total hydrogen and carbon monoxide. Preferably, the carbon dioxide concentration in the off-gas after carbon dioxide removal is between about 2 and 40, more preferably between about 5 or 10 and 20, mole percent. The off-gas after carbon dioxide removal may contain at least about 5, and often about 10 to 20, mole percent nitrogen.

If desired, a portion of the carbon dioxide dissolved in the liquid phase of the aqueous menstruum can be removed. Any convenient unit operation for carbon dioxide removal can be used, but the preferred operation is separation by reducing the pressure to atmospheric or lower pressure to flash carbon dioxide gas from the liquid phase.

DESCRIPTION

Figure 1:
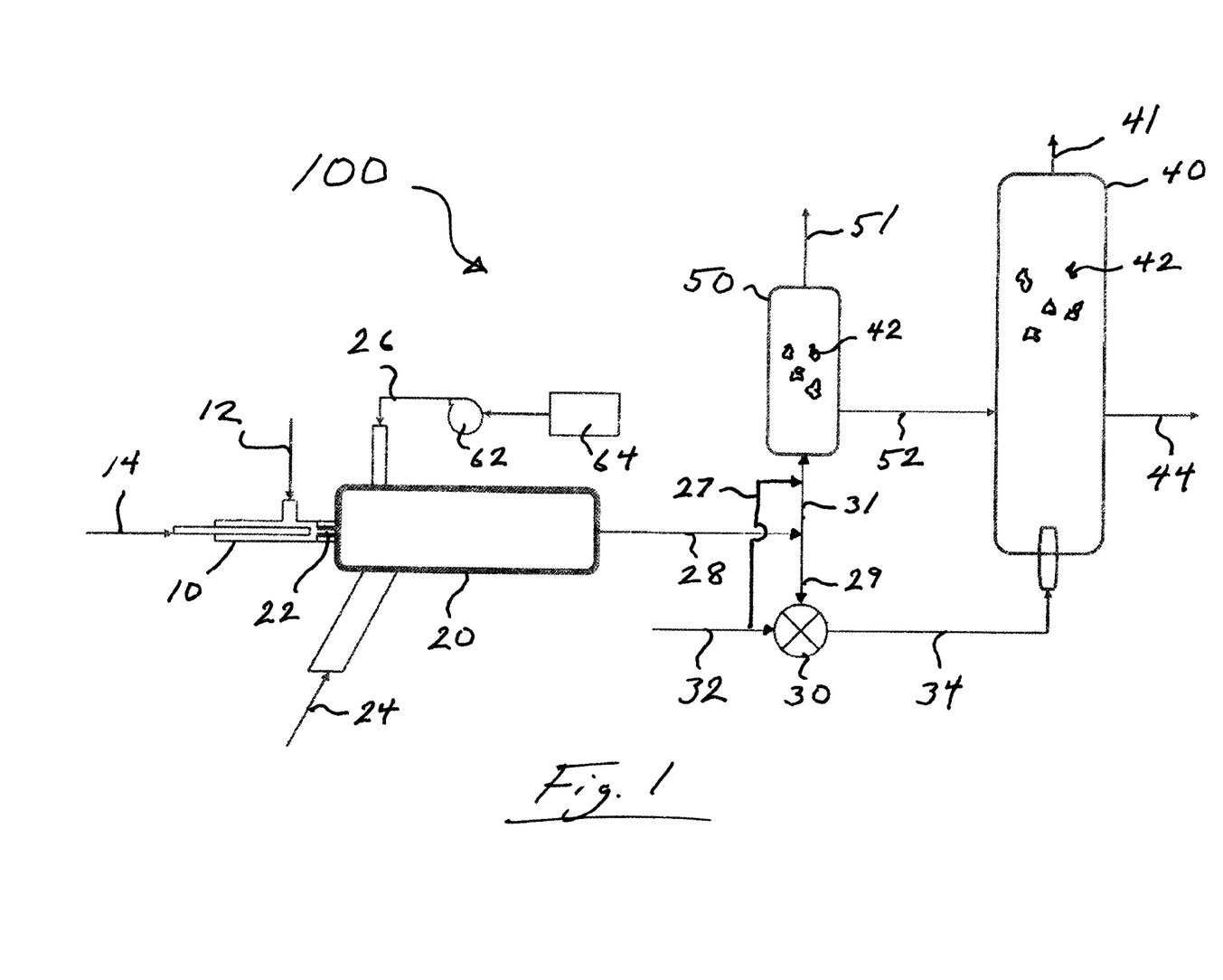
FIG. 1 is a schematic drawing of a sulfide generation system to convert feed gas to liquid product in accordance with the present invention.

FIG. 1 is a schematic drawing of a sulfide generation system to convert feed gas to liquid product in accordance with the present invention. A general understanding of the invention and its application may be facilitated by reference to FIG. 1. FIG. 1 is a schematic depiction of an apparatus generally designated as 100 suitable for practicing the processes of this invention. FIG. 1 omits minor equipment such as pumps, compressors, valves, instruments and other devices the placement of which and operation thereof are well known to those practiced in chemical engineering, and also omits ancillary unit operations. The sulfide generation system 100 includes a partial oxidation reformer 20, a mixer 30, and a production fermentor 40. The partial oxidation reformer 20 can be the partial oxidation reformer used in the production of syngas for bioconversion, e.g., the partial oxidation reformer converting methane to CO, $H_2/CO_2$.

The partial oxidation reformer 20 is operable to partially oxidize high-temperature gas stream 22, input gas stream 24, and molten sulfur stream 26 to generate sulfide gas stream 28.

The quantity of the molten sulfur in the molten sulfur stream 26 provided to the partial oxidation reformer 20 is small relative to the gas feed (high-temperature gas stream 22 and input gas stream 24) and the molten sulfur stream 26 reacts immediately with hydrogen in the high-temperature gas stream 22 and input gas stream 24 to form hydrogen sulfide. The molten sulfur stream 26 can be delivered to the partial oxidation reformer 20 by a metering pump 62 attached to a molten sulfur storage tank 64.

In one embodiment, the sulfide generation system 100 can also include an oxygen burner 10 operably connected to the partial oxidation reformer 20 to provide the high-temperature gas stream 22 to the partial oxidation reformer 20 at a high injection velocity. The oxygen burner 10 is operable to combust oxygen stream 12 and burner gas stream 14 to generate the high-temperature gas stream 22. The burner gas stream 14 preferably contains methane. In one example, the burner gas stream 14 is natural gas. In another example, the burner gas stream 14 includes at least one of hydrogen and $C_1$ to $C_4$ hydrocarbons.

In one example, the high-temperature gas stream 22 contains oxygen. In one example, the input gas stream 24 contains a carbonaceous fuel, such as methane, syngas, natural gas, and combinations thereof. The input gas stream 24 can be syngas, such as raw syngas from a gasifier. In another example, the input gas stream 24 is natural gas containing methane used as a supplemental feed to fermentors, such as a production or seed fermentor. Where the input stream comprises methane, the methane content in the input gas stream 24 can range from 10 percent to 100 percent by volume. The partial oxidation of the input gas stream 24 with the oxygen from high-temperature gas stream 22 at a temperature greater than 1000° C. substantially converts the input gas stream 24 to CO, $H_2/CO_2$. The oxygen stream 12 can be pure or substantially pure. In one example, the sulfide gas stream 28 contains hydrogen sulfide, CO, $CO_2$, and $H_2$.

The mixer 30 provides fine control of the hydrogen sulfide concentration in the mixed gas stream 34 provided to the production fermentors 40. The mixer 30 is operably connected to receive all or a portion of the sulfide gas stream 28 from the partial oxidation reformer 20 via a line 29. The mixer 30 is operable to mix the sulfide gas stream 28 with the feed gas stream 32 to generate the mixed gas stream 34. In one example, the mixer 30 is a static mixer. The mixed gas stream 34 has a predetermined hydrogen sulfide concentration as desired for a particular application. In one example, the predetermined hydrogen sulfide concentration is in the range from about 100 to 1000 ppm. The feed gas stream 32 can be reformed syngas derived from biomass or other carbonaceous feedstocks with toxic or undesirable impurities removed. The feed gas stream 32 can also include hydrogen sulfide derived from gasification reactions of the feedstock.

The production fermentor 40 contains microorganisms 42 and is operably connected to receive at least a portion of the mixed gas stream 34 from the mixer 30. The microorganisms 42 make use of the hydrogen sulfide in the mixed gas stream 34 for their metabolism, with the predetermined hydrogen sulfide concentration being selected to support the particular microorganism or microorganisms in use. The production fermentor 40 is operable to convert the mixed gas stream 34 to liquid product stream 44 through contact of the mixed gas stream 34 with the microorganisms 42. When the feed gas stream 32 is syngas, the liquid product stream 44 can be ethanol, propanol, or butanol. In one example, the input gas stream 24 is syngas and the liquid product stream 44 is a $C_1$ to $C_4$ oxygenated liquid product. Unconverted gas components exit the production fermentor 40 through stream 41.

In another embodiment, the sulfide generation system 100 can also include a seed fermentor 50 operably connected to the mixer 30. The seed fermentor 50 may be series of vessels in a seed train that produces a culture 52 as a seed broth to add to the production fermentors 40. The seed fermentor 50 is operable to receive a portion of the sulfide gas stream 28 via a line 31, and may optionally receive a portion of the feed gas stream 32 via a line 27, to grow a culture of the microorganisms 42 and to provide the culture via a line 52 to the production fermentor 40. The sulfide gas stream 28 can be split between the seed fermentor 50 and the mixer 30 to provide the sulfide gas to the seed fermentor 50 and the mixed gas to the production fermentor 40. Unconverted gas components exit the seed fermentor 50 through stream 51. The seed fermentor 50 requires a smaller portion of the sulfide gas stream 28 than that applied to the production fermentor 40 in the mixed gas stream 34.

Figure 2:
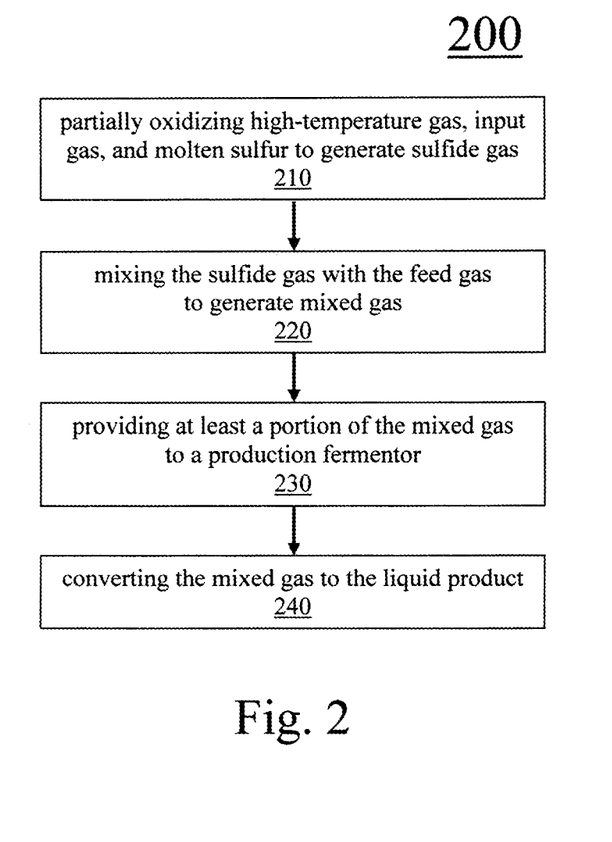
FIG. 2 is a flowchart for a sulfide generation process to convert feed gas to liquid product in accordance with the present invention.

FIG. 2 is a flowchart for a sulfide generation process to convert feed gas to liquid product in accordance with the present invention. In one embodiment, a sulfide generation process is performed with the sulfide generation system as shown in FIG. 1. Referring to FIG. 2, the process 200 includes partially oxidizing high-temperature gas, input gas, and molten sulfur to generate sulfide gas 210, the high-temperature gas containing oxygen, the input gas containing a carbonaceous fuel, preferably methane, and the sulfide gas containing hydrogen sulfide, CO, $CO_2$, and $H_2$; mixing the sulfide gas with the feed gas to generate mixed gas 220 having a predetermined hydrogen sulfide concentration; providing at least a portion of the mixed gas to a production fermentor 230 containing microorganisms; and converting the mixed gas to the liquid product 240 by contact with the microorganisms. In one example, the input gas is selected from methane, syngas, and natural gas. In another example, the partially oxidizing high-temperature gas, input gas, and molten sulfur 210 is performed at a temperature greater than about 1000° C. In yet another example, the predetermined hydrogen sulfide concentration is in the range from about 100 to 1000 ppm. In yet another example, the feed gas is syngas (syngas feed) and the liquid product is selected from ethanol, propanol, and butanol. In one example, the input gas is syngas and the liquid product is a $C_1$ to $C_4$ oxygenated liquid product.

In one embodiment, the process 200 can also include combusting oxygen and burner gas to generate the high-temperature gas, the burner gas containing at least one of hydrogen, and $C_1$ to $C_4$ hydrocarbons. In one example, the burner gas is methane. In another example, the burner gas is natural gas.

In another embodiment, the process 200 can also include providing another portion of the mixed gas to a seed fermentor; growing a culture of the microorganisms in the seed fermentor; and providing the culture to the production fermentor.

Example

The following prophetic example is meant to illustrate and not to limit the scope of the invention. The process and operation of FIG. 1 will be described in the context of the recovery and production of ethanol. The reference to FIG. 1 encompasses a description of a computer simulation of a process producing approximately 3760 kilograms of ethanol per hour. The process is readily adaptable to making other oxygenated products, such as acetic acid, butanol, propanol, butyric acid, isopropanol, and the like. Reference numbers refer to the elements of FIG. 1.

Oxygen at a mass flow rate of about 309.9 kg/hr from oxygen stream 12 and natural gas at a rate of about 25.9 kg/hr as burner gas from burner gas stream 14 are provided to an oxygen burner 10. The resulting reaction provides high-temperature gas stream 22 at a mass flow rate of approximately 335.7 kg/hour. The high-temperature gas stream 22 passes through a nozzle into the partial oxidation reformer 20. The high-temperature gas stream 22 includes a mixture of $CO_2$, $O_2$, and $H_2O$ in molar ratio of 1:4:2, respectively.

The high-temperature gas stream 22 is mixed with syngas (having the relative composition given in Table 1) as input gas stream 24 and molten sulfur stream 26 within the partial oxidation reformer. The syngas is provided at the rate of approximately 1,377.1 kg/hr and the molten sulfur is provided at the rate of approximately 9.1 kg/hr. The sulfide gas stream 28 is generated at 1400° C. and then cooled to approximately 40° C.; the flow rate of this stream is approximately 1,228 kg/hr and has the relative composition given in Table 2. The sulfide gas stream 28 is provided to the mixer 30 at a temperature of approximately 40° C.

TABLE 1

Input Syngas

| Component | Composition |
|---|---|
| $H_2$ | 12.3% |
| CO | 26.1% |
| $CO_2$ | 6.3% |
| $H_2O$ | 41.8% |
| $N_2$ | 0.5% |
| $O_2$ | 0.0% |
| $CH_4$ | 8.9% |
| $H_2S$ | 80 ppmv |

TABLE 2

Cooled Sulfide Gas

| Component | Composition |
|---|---|
| $H_2$ | 42.3% |
| CO | 42.9% |
| $CO_2$ | 12.3% |
| $H_2O$ | 1.5% |
| $N_2$ | 0.6% |
| $O_2$ | 0.0% |
| $CH_4$ | 0.0% |
| $H_2S$ | 4000 ppmv |

The sulfide gas stream 28 is mixed with clean reformed syngas as feed gas stream 32 at the mixer 30 to generate mixed gas stream 34 having the desired predetermined hydrogen sulfide concentration. The reformed syngas is cooled and cleaned with scrubber and provided at temperature of about 10° C., at the rate of approximately 8,470 kg/hr, and has the composition given in Table 3. Mixer 30 mixes the sulfide gas stream 28 with the reformed syngas stream (feed gas stream 32) and produces the mixed gas stream 34 at the rate of approximately 9,691 kg/hr and with an approximate composition in Table 4.

TABLE 3

Feed Syngas

| Component | Composition |
|---|---|
| $H_2$ | 47.6% |
| CO | 48.1% |
| $CO_2$ | 3.5% |
| $H_2O$ | 0.1% |
| $N_2$ | 0.7% |
| $O_2$ | 0.0% |
| $CH_4$ | 0.0% |
| $H_2S$ | 80 ppmv |

TABLE 4

Mixed Gas

| Component | Composition |
|---|---|
| $H_2$ | 47.0% |
| CO | 47.5% |
| $CO_2$ | 4.5% |
| $H_2O$ | 0.2% |
| $N_2$ | 0.7% |
| $O_2$ | 0.0% |
| $CH_4$ | 0.0% |
| $H_2S$ | 500 ppmv |

The production fermentor 40 retains a suspended culture of the microorganism *Clostridium coskatii* that converts the entering mixed gas stream into liquid product such that approximately 3,760 kg/hr of ethanol are recovered through liquid product stream 44.

Those skilled in the art will appreciate that the injection rate of the molten sulfur stream 26 into the partial oxidation reformer 20 can be selected as desired to produce desired hydrogen sulfide concentration in the sulfide gas stream 28 and thus the predetermined hydrogen sulfide concentration in the mixed gas stream 34. The feed rate of the feed gas stream 32 to the mixer 30 can also be controlled to produce the desired predetermined hydrogen sulfide concentration in the mixed gas stream 34.

While the embodiments of the invention disclosed herein are presently considered to be preferred, various changes and modifications can be made without departing from the scope of the invention. The scope of the invention is indicated in the appended claims, and all changes that come within the meaning and range of equivalents are intended to be embraced therein.

The invention claimed is:

1. A process to convert feed gas to liquid product, the process comprising:
   partially oxidizing high-temperature gas, input gas, and molten sulfur to generate sulfide gas, the high-temperature gas containing oxygen, the input gas containing a carbonaceous fuel, and the sulfide gas containing hydrogen sulfide, CO, $CO_2$, and $H_2$;
   mixing the sulfide gas with the feed gas to generate mixed gas having a predetermined hydrogen sulfide concentration;
   providing at least a portion of the mixed gas to a production fermentor containing microorganisms; and
   converting the mixed gas to the liquid product by contact with the microorganisms.

2. The process of claim 1 further comprising combusting oxygen and burner gas to generate the high-temperature gas, the burner gas comprising at least one of hydrogen and $C_1$ to $C_4$ hydrocarbons.

3. The process of claim 2 wherein the burner gas comprises natural gas.

4. The process of claim 1 further comprising:
providing another portion of the mixed gas to a seed fermentor;
growing a culture of the microorganisms in the seed fermentor; and
providing the culture to the production fermentor.

5. The process of claim 1 wherein the input gas is selected from the group consisting of methane, syngas, and natural gas.

6. The process of claim 1 wherein the partially oxidizing high-temperature gas, input gas, and molten sulfur is performed at a temperature greater than about 1000° C.

7. The process of claim 1 wherein the predetermined hydrogen sulfide concentration is in the range from about 100 to 1000 ppm.

8. The process of claim 1 wherein the feed gas comprises syngas and the liquid product is selected from the group consisting of ethanol, propanol, and butanol.

9. A process to convert syngas feed to a $C_1$ to $C_4$ oxygenated liquid product, the process comprising:
combusting oxygen and burner gas to generate high-temperature gas;
partially oxidizing the high-temperature gas, syngas, and molten sulfur to generate sulfide gas, the high temperature gas containing oxygen, and the sulfide gas containing hydrogen sulfide, $CO$, $CO_2$, and $H_2$;
mixing the sulfide gas with the syngas feed to generate mixed gas having a predetermined hydrogen sulfide concentration;
providing at least a portion of the mixed gas to a production fermentor containing microorganisms; and
converting the mixed gas to the $C_1$ to $C_4$ oxygenated liquid product by contact with the microorganisms.

10. The process of claim 9 further comprising:
providing another portion of the mixed gas to a seed fermentor;
growing a culture of the microorganisms in the seed fermentor; and
providing the culture to the production fermentor.

11. The process of claim 9 wherein the partially oxidizing the high-temperature gas, syngas, and molten sulfur is performed at a temperature greater than about 1000° C.

12. The process of claim 9 wherein the predetermined hydrogen sulfide concentration is in the range from about 100 to 1000 ppm.

13. The process of claim 9 wherein the $C_1$ to $C_4$ oxygenated liquid product is ethanol.

* * * * *